US012797027B2

(12) United States Patent
Vija et al.

(10) Patent No.: US 12,797,027 B2
(45) Date of Patent: Nov. 17, 2026

(54) MINI-SPECT AS DOSIMETER

(71) Applicant: Siemens Medical Solutions USA, Inc., Malvern, PA (US)

(72) Inventors: Alexander Hans Vija, Evanston, IL (US); Miesher Rodrigues, Buffalo Grove, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1084 days.

(21) Appl. No.: 17/905,421

(22) PCT Filed: Sep. 10, 2020

(86) PCT No.: PCT/US2020/070520
§ 371 (c)(1),
(2) Date: Sep. 1, 2022

(87) PCT Pub. No.: WO2022/055539
PCT Pub. Date: Mar. 17, 2022

(65) Prior Publication Data

US 2023/0120478 A1 Apr. 20, 2023

(51) Int. Cl.
*A61B 6/00* (2006.01)
*A61B 6/03* (2006.01)
*G01T 1/02* (2006.01)

(52) U.S. Cl.
CPC ............ *A61B 6/5217* (2013.01); *A61B 6/037* (2013.01); *G01T 1/026* (2013.01)

(58) Field of Classification Search
CPC ........ A61B 6/5217; A61B 6/037; G01T 1/026
See application file for complete search history.

(56) References Cited

U.S. PATENT DOCUMENTS

| | | |
|---|---|---|
| 4,859,853 A | 8/1989 | Kronenberg |
| 5,274,239 A | 12/1993 | Lane et al. |

(Continued)

FOREIGN PATENT DOCUMENTS

| | | |
|---|---|---|
| CN | 103099634 | 5/2013 |
| CN | 104784770 | 7/2015 |

(Continued)

OTHER PUBLICATIONS

BIODEX "Dose Calibrators" https://m.biodex.com/nuclear-medicine/products/dose-calibrators pp. 1-2. Retrieved on Aug. 12, 2020.

(Continued)

*Primary Examiner* — Uzma Alam
*Assistant Examiner* — Fani Polyzos Boosalis

(57) ABSTRACT

For dosimetry, a miniaturized nuclear imaging system with a solid-state detector is used to determine the activity and/or injected dose for a radiopharmaceutical. By being sized to scan the syringe or vial, the injected dose may be determined using the solid-state detector with greater accuracy than current dose calibrators and with less frequent use of a calibrated or standardized source. This miniaturized nuclear imaging system reconstructs activity in a same way as the nuclear imaging system scanning a patient, so may be used to calibrate the dose model. A tissue mimicking object with a solid-state dosimeter measures dose from the radiopharmaceutical, which dose is used to calibrate the dose model.

19 Claims, 3 Drawing Sheets

(56) References Cited

U.S. PATENT DOCUMENTS

| | | | | | |
|---|---|---|---|---|---|
| 5,572,027 | A * | 11/1996 | Tawil | G01T 1/026 250/389 |
| 8,577,103 | B2 | 11/2013 | Vija | |
| 8,675,936 | B2 | 3/2014 | Vija | |
| 9,171,353 | B2 | 10/2015 | Vija | |
| 9,326,742 | B2 * | 5/2016 | Hirschman | A61B 6/037 |
| 9,332,907 | B2 | 5/2016 | Vija | |
| 9,364,192 | B2 | 6/2016 | Vija | |
| 9,910,162 | B2 | 3/2018 | Bhattacharya | |
| 10,245,002 | B2 | 4/2019 | Bhattacharya | |
| 11,642,093 | B2 * | 5/2023 | Vija | G01T 1/24 250/370.07 |
| 2007/0235641 | A1 | 10/2007 | Allberg | |
| 2009/0236536 | A1 * | 9/2009 | Lamb | A61N 5/00 250/252.1 |
| 2013/0015361 | A1 | 1/2013 | Bouton | |
| 2013/0045421 | A1 | 2/2013 | Kobino et al. | |
| 2013/0131422 | A1 | 5/2013 | Vosniak et al. | |
| 2013/0261440 | A1 | 10/2013 | Georgi et al. | |
| 2014/0371580 | A1 | 12/2014 | Bhattacharya | |
| 2015/0196268 | A1 | 7/2015 | Bhattacharya | |
| 2016/0136453 | A1 * | 5/2016 | Agamaite | A61N 5/1001 600/4 |
| 2017/0172527 | A1 | 6/2017 | Uber, III | |
| 2018/0301233 | A1 | 10/2018 | Quirico et al. | |
| 2019/0038252 | A1 | 2/2019 | Bhattacharya | |
| 2019/0357872 | A1 | 11/2019 | Ding et al. | |

FOREIGN PATENT DOCUMENTS

| | | | | |
|---|---|---|---|---|
| CN | 106110518 | | 11/2016 | |
| CN | 107550511 | | 1/2018 | |
| CN | 110599472 | | 12/2019 | |
| EP | 1992965 | A2 | 11/2008 | |
| EP | 3254624 | | 12/2017 | |
| JP | H01129199 | | 5/1989 | |
| JP | 2004317140 | A | 11/2004 | |
| JP | 2009098131 | A | 5/2009 | |
| JP | 2010256176 | A | 11/2010 | |
| JP | 2017161380 | | 9/2017 | |
| JP | 2017219530 | A | 12/2017 | |
| WO | 2013045421 | A1 | 4/2013 | |
| WO | WO-2019172997 | A1 * | 9/2019 | G01T 1/02 |

OTHER PUBLICATIONS

PSTAR and ASTAR "Databases for Protons and Helium Ions" https://www.physics.nist.gov/PhysRefData/Star/Text/programs.html pp. 1-3. Retrieved on Aug. 18, 2020.
Stabin, M., and A. B. Brill. "Physics applications in nuclear Medicine: Progress on many fronts." The Journal of Nuclear Medicine 46.2 (2005): 16N.
Stabin, Michael G. "Update: the case for patient-specific dosimetry in radionuclide therapy." Cancer biotherapy & radiopharmaceuticals 23.3 (2008): 273-284.
Stabin, Michael G., and Jeffry A. Siegel. "Physical models and dose factors for use in internal dose assessment." Health physics 85.3 (2003): 294-310.
Stabin, Michael G., Richard B. Sparks, and Eric Crowe. "OLINDA/EXM: the second-generation personal computer software for internal dose assessment in nuclear medicine." Journal of nuclear medicine 46.6 (2005): 1023-1027.
Stabin, Michael. "Nuclear medicine dosimetry." Physics in Medicine & Biology 51.13 (2006): R187.
University of San Diego "Radionuclide Data Sheet" https://ehs.ucsd.edu/rad/radionuclide/Lu-177.pdf pp. 1-1. Retrieved on Aug. 18, 2020.
Watson, Evelyn E., Michael G. Stabin, and Jeffry A. Siegel. "MIRD formulation." Medical physics 20.2 Pt 2 (1993): 511-514.
International Search Report for corresponding application No. PCT/US2020/070520, dated May 26, 2021.
Adler Stephen et al:; "Development and performance measurements of a micro-dose calibrator," ; Journal of Nuclear Medicine May 2018; 59.

* cited by examiner

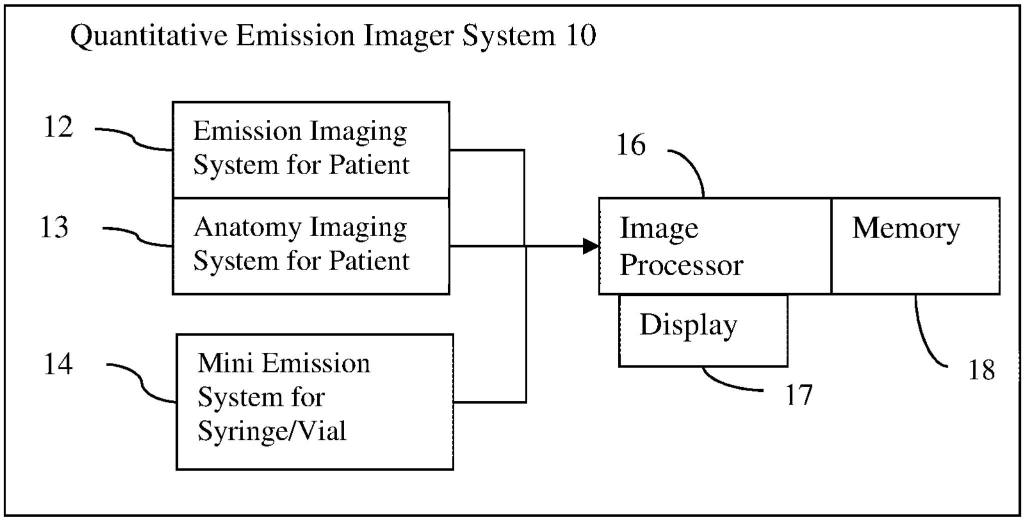
FIG. 1
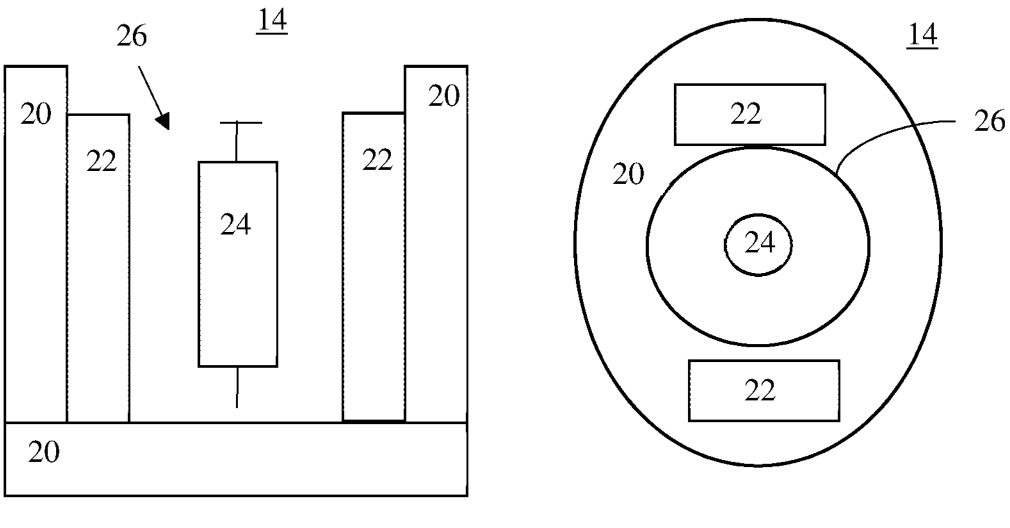
FIG. 2A
FIG. 2B

MINI-SPECT AS DOSIMETER

BACKGROUND

The present embodiments relate to emission tomography or nuclear imaging. An injected radiopharmaceutical emits gamma rays (in the case of single-photon-emission-computer-tomography (SPECT) imaging) or positrons that annihilate with electrons to produce gamma rays (in the case of positron-emission-tomography (PET) imaging). A detector system located outside the patient detects the emitted gamma rays and reconstructs images based on the detected emissions.

In theranostics, the radiopharmaceutical is used as a therapeutic agent. Emitted radiation applies a therapeutic dose to tracer-targeted tissue within the volume. Nuclear imaging is used to determine the dose applied to a patient. Internal dosimetry, such as medical internal radiation dose (MIRD), is the estimation of energy deposited to tissue due to uptake of the radioactive substance in the patient. Activity over time in the patient, such as from nuclear imaging of the patient at multiple timepoints (e.g., over a day or two), and a measurement of the injected dose are used with a general dose model indicate the internal dose. The general dose model may be inaccurate.

A dose calibrator based on a gas chamber detector is used to measure the dose (activity or activimeter) contained in the syringes and vials pre- and post-injection, but the gas chamber has a nonlinear sensitivity to energy response. Dose calibrators, despite calibration, shows errors in excess of 10% unless a calibrated source is used to compute the correction factor. Calibrated sources are used for calibration and cross calibration between dose calibrators and the nuclear imaging system to allow for accurate and precise dose determination. The use and shipping of calibrated radioactive sources, required for each hospital, is complicated and costly.

SUMMARY

By way of introduction, the preferred embodiments described below include methods, systems, instructions, and computer readable storage media for dosimetry. A miniaturized nuclear imaging system with a solid-state detector is used to determine the activity and/or injected dose for a radiopharmaceutical. By being sized to scan the syringe or vial, the injected dose may be determined using the solid-state detector with greater accuracy than current dose calibrators and with less frequent use of a calibrated or standardized source. This miniaturized nuclear imaging system reconstructs activity in a same way as the nuclear imaging system scanning a patient, so may be used to calibrate the dose model. A tissue mimicking object with a solid-state dosimeter measures dose from the radiopharmaceutical, which dose is used to calibrate the dose model.

In a first aspect, a method is provided for determining injected dose. First activity of a radiopharmaceutical in a syringe or vial is measured with the syringe or vial in a nuclear imaging system having a solid-state detector and sized to scan the syringe or vial without fitting a patient. Second activity of remaining amounts of the radiopharmaceutical in the syringe or vial is measured with the nuclear imaging system after injection into the patient. An injected dose (activity) is determined from the first activity and the second activity.

In various embodiments, the solid-state detector is formed from semiconductor material, the nuclear imaging system is sized to fit the syringe or vial in a hole less than 3 inches by 3 inches, and/or the nuclear imaging system has at least one handle and is sized to be carriable by a person using the handle.

In one embodiment, single photon emission computed tomography scans of the radiopharmaceutical in the syringe or vial are performed by the nuclear imaging system to measure the activities. The first and second activities are reconstructed from emissions detected in the scans.

The injected dose may be determined without use of a dose calibrator for the radiopharmaceutical for a given patient. For example, the first activity is measured over time, and the second activity is measured over time. A first model is fit to the first activity over time, and a second model is fit to the second activity over time. A first dose is derived from the first model as fit, and a second dose is derived from the second model as fit. The injected dose is calculated from a difference between the first and second doses.

A standard or calibrated source is not needed for each patient use. The nuclear imaging system may be calibrated in-frequently from emission detection from a standardized source in the nuclear imaging system.

The nuclear imaging system may be used to calibrate the dose model. The first activity is measured where a tissue mimicking object including a solid-state dosimeter is in the nuclear imaging system with the syringe or vial. The solid-state dosimeter measures a first dose. The dose model is calibrated for the radiopharmaceutical with the first dose. The dose model is one of a physics model, dose kernel model, or transfer model.

The injected dose and/or calibrated dose model are used to calculate the internal dose for a patient. The miniaturized nuclear imaging system may be used to determine the isotope of the radiopharmaceutical and/or the form factor for the syringe or vial. The activity of the radiopharmaceutical in the syringe or vial is measured using an emissions scan by the nuclear imaging system. The isotope or form factor may be determined from the emission scan, avoiding or confirming user input of such information.

In a second aspect, a dosimeter is provided for medical nuclear imaging. A cavity is configured to hold a syringe or vial. A semiconductor detector adjacent the cavity is configured to detect emissions from within the syringe or vial within the cavity. An image processor is configured to determine a dose for the syringe or vial from the emissions.

In one embodiment, the cavity has an opening of 3 inches by 3 inches or less through which the syringe or vial is placeable into the cavity. In another embodiment, the semiconductor detector is a pair of solid-state detectors on opposite sides of the cavity. In other embodiments, the image processor is configured to determine the dose from a reconstruction of activity in the syringe or vial. The reconstruction is from the emissions detected by the semiconductor detector.

The cavity may allow for a tissue mimicking object with a solid-state dosimeter. The tissue mimicking object is positionable within the cavity. The image processor is configured to calibrate a dose model from signals from the solid-state dosimeter.

In a third aspect, a method is provided for calibration of a dose model in nuclear imaging. Emissions from a radiopharmaceutical to be injected into a patient are detected with a solid-state detector. The radiopharmaceutical is within a cavity adjacent to the solid-state detector during the detecting. A first dose is measured with a solid-state dosimeter in a tissue mimicking object. The tissue mimicking object is in the cavity during the detecting and measuring. A dose model is calibrated with the first dose from the solid-state dosimeter and a second dose derived from the emissions.

In one embodiment, the second dose is determined from a reconstruction of activity over time of the detected emissions. An internal dose for a patient is calculated after injection of the radiopharmaceutical with the dose model as calibrated.

In a fourth aspect, a method is provided for determining injected dose. A nuclear imaging system having a solid-state detector images a radiopharmaceutical in a syringe or vial. Activity of the radiopharmaceutical in the syringe or vial is computed from the imaging. An isotope of the radiopharmaceutical in the syringe or vial is determined from the imaging of the radiopharmaceutical in the syringe or vial. Dose in a patient is estimated based on the activity and the isotope.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a block diagram of one embodiment of a quantitative emission imager system using a miniaturized emission system for determining injected dose and/or for dose model calibration;

FIGS. 2A and 2B are side and top cross-sectional views of a miniaturized emission system;

DETAILED DESCRIPTION OF THE DRAWINGS AND PRESENTLY PREFERRED EMBODIMENTS

Figure 3:
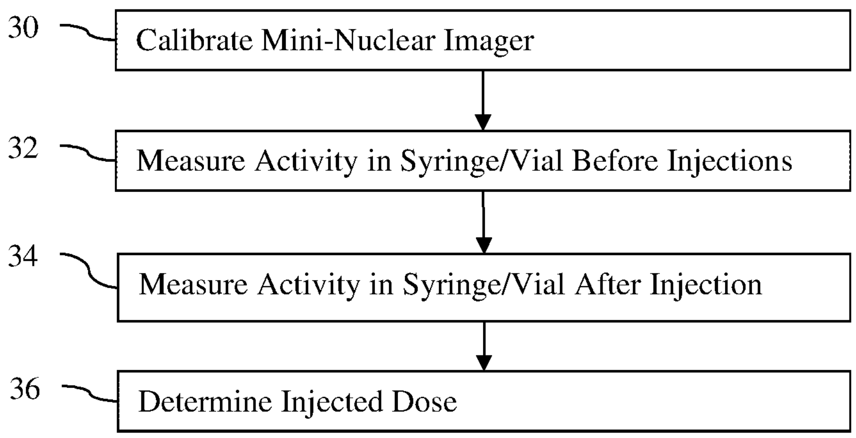
FIG. 3 is a flow chart diagram of one embodiment of a method for determining injected dose.

A calibrated Mini-SPECT or PET is used as a standardized dosimeter for accurate measurements of activity in syringes and vials. This mini-nuclear imaging system may be used for integrated dose calibration. A national institute of standards and technology (NIST) traceable calibration of activity and/or dosimetry may be provided for any of various isotope compounds or mixtures and form factors (type of syringe and/or vial).

Proportional gas chambers or scintillator materials are typically used as indirect converters. Proportional gas chambers or scintillator materials have known non-linearity energy response, poor or no energy resolution capabilities, and require calibration with multiple photon energies. Instead of using a proportional gas chamber or scintillator material, a portable solid-state mini SPECT or PET system with spectroscopic high energy resolution images syringes and vials to estimate the activity content and doses. Solid-state sensors (or detectors) may be more easily calibrated without the issues encountered in gas chambers and scintillators. The imaging system for the patient and the dosimeter (e.g., mini-SPECT) have similar linear energy responses. The mini-SPECT or PET may replace existing dosimeters and requires fewer standard or calibrated sources in every day use.

Since the image geometry is fixed and rather standardized, any method of tomographic reconstruction to estimate the activity and dose (e.g., activity as mCl or MBq as decay per second per unit of volume and/or for the total volume) in the syringe and vials may be used. The mini-nuclear imaging system allows for activity and dose model (e.g., dose kernel) calibration, which may not be possible with a gas chamber or scintillation crystal-based dosimeter. Solid-state dosimeters (e.g., diamond detectors) in a bath or another tissue mimicking object are used to estimate the dose given the amount of activity present, allowing for the calibration of image-based dosimetry to be as accurate as existing methods with less or no need of user intervention.

By using imaging, the isotope or mix of isotopes may be identified. This information allows for calibration and/or deposited dose estimating to be based on measurements, automating both determination of injected dose or activity and isotope or mixture being used. The calibration and energy deposition (e.g., dosimetry for the patient) are reliably provided in combination without requiring or relying on manual input of the isotope.

FIG. 1 shows one embodiment of a quantitative emission imager system 10. The system 10 determines the dose to which a patient is subjected from a radiopharmaceutical. Sets of emission data from different timepoints or scans of the patient are used to estimate the dose. By reconstructing the dose rather than time specific uptake or tracer distribution, the dose applied to the patient during a therapeutic cycle or over multiple cycles is provided for confirming dosage in therapy and/or planning further therapy. In alternative embodiments, the dose is determined as a calculation from reconstructed activity over time or the dose is determined by reconstructing the dose in one reconstruction.

The system 10 includes an image processor 16, an emission imaging system 12, anatomy imaging system 13, a miniaturized emission system 14, a memory 18, and a display 17. Additional, different, or fewer components may be provided. For example, the anatomy imaging system 13 is not provided where dose is estimated without anatomical information. In one embodiment, the image processor 16, memory 18, and/or display 17 are part of one of the emission imaging system 12 or the anatomy imaging system 13. In alternative embodiments, the image processor 16, memory 18, and/or display 17 are provided as a workstation, server, or computer separate from the imaging systems 12, 14. The memory 18 is part of a computer or workstation with the image processor 16 or is a remote database, such as a picture archiving and communications system (PACS).

The anatomy imaging system 13 is a computed tomography (CT), magnetic resonance (MR), ultrasound, or other diagnostic medical imaging system. The anatomy imaging system 13 scans a patient with x-rays, ultrasound, or electric pulses to image the anatomy of the interior of the patient. A source transmits energy to the patient. A detector receives signals responsive to the transmitted energy. Any now known or later developed anatomy imaging system 13 may be used. While "imaging" or "image" is used herein, the anatomy imaging system 13 may be used to acquire anatomy data representing the patient without generating or displaying an image on a display device.

In one embodiment, the anatomy imaging system 13 is a CT system. An x-ray source and detector are mounted on a moveable gantry. The x-ray source generates x-rays, some of which pass through the patient. The detector detects the transmitted x-rays that pass through the patient. The energy used, timing, scan angles, and/or other aspects of the CT scan are set for a patient and used to scan a volume or other region of the patient. CT is used to generate a representation of the anatomy of the patient.

The emission imaging system 12 is any now known or later developed nuclear imaging system, such as a SPECT or PET scanner. The emission imaging system 12 includes a detector for detecting emitted radiation from within the patient. For SPECT, a gamma camera is used to detect. The detector detects photon emissions. A given detector may detect a sequence of events from the same or different locations of the patient.

The emission tomography system 12 is configured by software, firmware, and/or hardware to detect emissions. The emission tomography system 12 detects emissions from the same patient but during different imaging sessions. Each imaging session provides a complete scan of the patient, such as positioning a gamma camera at different locations relative to the patient and detecting emissions at each position during a dwell time. The patient may leave the emission tomography system 12 (e.g., get up off of the bed) between the different imaging sessions. The imaging sessions may be performed at different periods distributed over hours or days while the patient is being dosed by an internal radiopharmaceutical. The imaging sessions occur during a therapy cycle and/or over multiple therapy cycles. The imaging sessions may be over a period that is less than an entire cycle. For a same cycle, the patient is subject to therapy from a given application or dosage of a radiotracer during the different imaging sessions. For each cycle, a different application of the radiotracer is used.

The memory 18 is a random-access memory, graphics processing memory, video random access memory, system memory, cache memory, hard drive, optical media, magnetic media, flash drive, buffer, database, combinations thereof, or other now known or later developed memory device for storing data. The memory 18 stores detected emissions (e.g., PET or SPECT detected event data), signals from anatomy scanning (e.g., CT data), zone information, segmentation information, partial volume effect, smoothing filter coefficients, test activity, reconstructed activity, dose, biodistribution, calibration, and/or reconstruction information. The memory 18 stores data as processed, such as storing a segmentation, calibration, forward projection of the assigned test activities, reconstruction from detected emissions, image objects, dose, a rendered image, and/or other information.

The memory 18 or other memory is a non-transitory computer readable storage medium storing data representing instructions executable by the programmed image processor 16 for determining dose or dose model calibration. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 17 is a monitor, LCD, plasma, touch screen, printer, or other device for displaying an image for viewing by a user. The display 17 shows one or more images representing dose, such as accumulated dose at a given time for a treatment cycle. Other images may be output, such as an image of function (i.e., representing the activity of the reconstructed object), such as uptake or activity concentration. The dose image is a quantitative image. The function image is a quantitative or qualitative SPECT or PET image. The image may be a volume rendering, a multi-planar reconstruction, a cross-section, and/or other image from a final image object. The image represents a distribution in the patient based on detected emissions from the emission imaging system 12. Alternatively or additionally, the display 17 displays an image of injected dose or spatial distribution of activity in the syringe or vial.

The image processor 16 is a general processor, central processing unit, control processor, graphics processor, digital signal processor, application specific integrated circuit, field programmable gate array, amplifier, comparator, time-to-digital converter, analog-to-digital converter, digital circuit, analog circuit, timing circuit, combinations thereof, or another now known or later developed device for reconstructing from detected emissions, determining dose, and/or calibrating a dose model. The image processor 16 is a single device or multiple devices operating in serial, parallel, or separately. The image processor 16 is specifically designed or provided for dose determination or model calibration but may be a main or general processor of a computer, such as a laptop or desktop computer, or may be a processor for handling tasks in a larger system. The image processor 16 may perform other functions.

The image processor 16 is configurable. The image processor 16 is configured by software, firmware and/or hardware. Different software, firmware, and/or instructions are loaded or stored in memory 18 for configuring the image processor 16.

The image processor 16 is configured to calculate the dose applied to the patient. The injected dose may be estimated from the detected emissions from different times directly in parametric model reconstruction or from reconstructed activity distribution at different times. Multi-modal reconstruction may be used, such as using the anatomy information to reconstruct based, in part, on locations of different tissues.

The image processor 16 is configured to reconstruct a distribution of the dose from the radiotracer by fitting a parametric or dose model of half-life of the radiotracer to the detected emissions. The radiotracer kinetics are modeled, such as including diffusion (e.g., k1 and k2 diffusion). The radiation transport and ionizing radiation energy deposition is modeled by a parametric model used in reconstruction. The parametric model may include Monte Carlo or dose kernels for emission determination. The generation of the object model from the emissions data uses, in part, the parametric or dose model of the dose kinetics. The dose model may provide different values for variables for different types of tissue as fit in the reconstruction. Alternatively, different parametric models are used for different types of tissue.

The image processor 16 is configured to determine a dose from the dose model. The fit dose model outputs the dose based on the input detected emissions from different time points. The dose is output as an accumulated dose. The fit dose model may be used to determine the accumulated dose at any time. The reconstruction directly determines the dose, providing a distribution of dose. Alternatively, the dose is calculated from reconstructions of activity at different times. Any dose calculation process may be used.

The image processor 16 uses an injected dose and/or the dose model to determine the internal dose of the patient. The miniature emission imaging system 14 is used to determine the injected dose and/or to calibrate the dose model. The miniature emission imaging system 14 is used as a dosimeter for medical nuclear imaging.

FIGS. 2A and 2B show side and top cross-section views of the miniature emission imaging system 14. The system 14 includes side-walls 20 and one or more detectors 22 forming a cavity 26. Additional, different, or fewer components may be provided. For example, a gantry for moving the detectors 22 and/or collimators between the cavity 26 and the detectors 22 are provided. Collimators may be adjustable, such as automatically adapting to the isotope being used and/or patient treatment application. The collimator may be a rotating collimator and/or may cover any number of detectors 22. The collimator may provide step-wise or continuous aperture changes.

The side-walls 20 are shielding material to prevent or limit emissions from the syringe 24 or vial from passing out of the system 14. A lid, such as additional shielding may be provided. The shielding is lead or other material.

The detector 22 is a semiconductor detector. Any solid-state detector may be used, such as CZT, CdTe, HgI2, TlBr, GaAs, or other semiconductor materials. The semiconductor material has spectroscopic high energy resolution and may operate at room temperature or be cooled (e.g., cooling for HPGe detector).

One or more detectors 22 are provided. FIGS. 2A and 2B show two detectors 22 as flat substrates or plates on opposite sides of the cavity 26. Other shapes and/or arrangements may be provided. One, two, or more detectors 22 (emission sensors) are positioned inside the miniaturized emission imaging system 14. Additional, different, or fewer detectors 22 may be used, such as a ring of detectors around the cavity 26. The detectors 22 may be mounted to a gantry or other devices for moving the detectors 22. The gantry may move or the detectors 22 may be positioned based on images from scanning using the detectors 22 and/or based on an algorithm or artificial intelligence.

The detectors 22 are adjacent to the cavity 26, such as being within the cavity 26. The detectors 22 may be directly adjacent the cavity 26 or one or more layers of intervening material are provided, such as collimators. The detectors 22 are adjacent to the cavity 26 where the detectors 22 may detect emissions from within the cavity 26. The detectors 22 are configured (e.g., positioned) to detect emissions from within the syringe 24 or vial within the cavity 26.

The cavity 26 is cylindrical or prismoid. The cavity 26 is formed from the side-walls 20 and/or detectors 22. The cavity 26 is sized to hold a syringe 24 or vial. For example, the cavity 26 is sized to have an opening of 3×3 inches or less (e.g., 1-inch×1 inch or 2 inch by 1 inch) and sufficient height to enclose the syringe 24 or vial holding radiopharmaceutical for one or a few patient applications. The volume of the cavity may be less than 1 cubic foot.

Due to the small size of the cavity 26, the mini-emission imaging system 14 may have one or more handles placed on a housing or the shielding side-walls 20. The handle may be on a lid, which latches or screws onto the body to enclose the cavity 26. The overall size and weight may allow the system 14 to be carried, such as being the size of a 1-liter pitcher, 1-gallon jug, large coffee mug, briefcase, or luggage. The system 14 may be portable by being carried by one or two people. In other embodiments, the system 14 is fixed in place, such as being clamped or bolted to a floor, wall, or ceiling.

The syringe 24 or vial, such as a syringe 24 for a single dosage of radiopharmaceutical, may be placed into the cavity 26 through an opening, such as a top opening as shown in FIG. 2A. A holder, such as a plastic holder, may be provided. Alternatively, the cavity 26 is sized to hold the syringe 24 or vial upright or resting on its side with a pressure or frictional engagement. The syringe 24 or vial is positioned in the cavity 26 for PET or SPECT scanning using the detectors 22.

The image processor 16 is configured to determine the activity and/or dose from the radiopharmaceutical in the syringe 24 or vial. The radioisotope of the radiopharmaceutical emits gamma rays or positrons that result in generation of gamma rays. Some of these emissions are detected by the detectors 22. The image processor 16 counts the detected emissions. The locations of the emissions (e.g., lines of response) may be recorded. For PET, the coincidence (e.g., matched timing from two detectors on opposite sides of the syringe 24) may be determined and recorded with the lines of response. The energy level of the emissions may or may not be recorded. An emission scan of the syringe 24 or vial is performed, and the image processor 16 determines the activity or dose from the emissions scan.

The image processor 16 is configured to determine the dose from activity over time. The dose may be reconstructed, such as including the dose model in the reconstruction from emissions at different times. Alternatively, the activities at each of multiple times are reconstructed. The dose is determined from the reconstructed activities using the dose model. The reconstruction is the same as the reconstruction to be used on the patient and provides a two or three-dimensional distribution of activity or dose. Alternatively, the image processor 16 uses a pseudo-imaging reconstruction that integrates the counts of emissions to provide a global dose and/or activity (e.g., count over an area or volume) without determining a spatial variation or distribution of the activity or dose.

The mini-emission imaging system 14 may be used to determine activity and/or dose for the syringe 24 or vial before and after injection. The differences in activity or dose indicate the injected activity and/or dose. FIG. 3 represents one embodiment of a method for determining the injected activity and/or dose.

Figure 5:
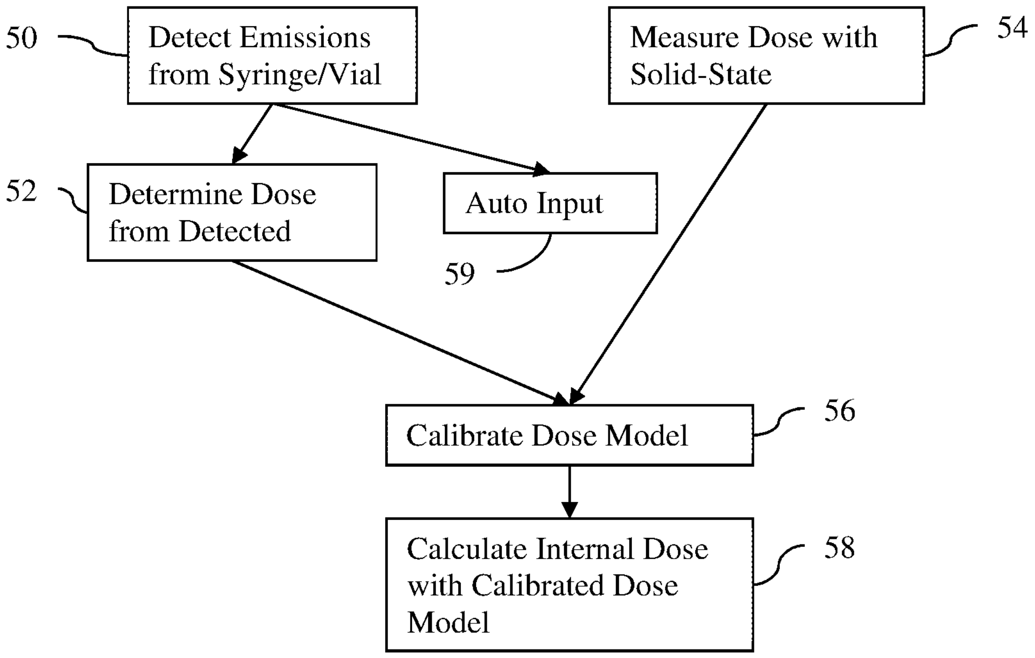
FIG. 5 is a flow chart diagram of one embodiment of a method for calibrating a dose model.

The mini-emission imaging system 14 may alternatively or additionally be used to calibrate the dose model. The generic function of uptake and washout of the radiopharmaceutical is a shark-fin like function, which is not known for an individual and depends on the specific individual and radiopharmaceutical injected. The dose is determined, in part, by modeling this generic function. Various dose models may be used, such as a physics model (e.g., Monte-Carlo-based model), a model formed from dose kernels, or a transport model of in-flow and out-flow. One or more characteristics of the model are set in calibration. To calibrate, the dose from the syringe 24 or model is determined by the emission scan using the dose model. The actual dose is measured using a solid-state dosimeter, such as a diamond detector in a tissue mimicking object, at the same time or a different time than the emission scan. The signals from the solid-state dosimeter are used to determine the actual dose. The two doses are compared. The setting for the dose model that minimizes the difference in the two doses is found, calibrating the dose model. Since the calibration is based on the radiopharmaceutical to be used with the patient and the dose model to be used to determine internal dose for the patient, the calibration may be accurate. FIG. 5 shows one embodiment of a method for calibrating the dose model.

FIG. 3 shows one embodiment a method for determining injected dose. The mini-emission imaging system 14 is used to determine the injected dose for a particular patient or instance. By directly measuring activity in a syringe or vial using a solid-state detector, the injected dose may be determined. The emission imaging system 14 allows for dose determination with more accuracy than a gas chamber dosimeter and with less need for calibration with multiple standardized, calibrated sources.

The method of FIG. 3 is implemented using the system 10 of FIG. 1, the mini-emission imaging system 14 with an image processor, and/or another device. For example, the mini-emission imaging system 14 scans the syringe or vial, and the image processor 16 determines the injected dose from results of the scanning.

The method is performed in the order shown (numerical or top to bottom), but other orders may be used. Additional, different, or fewer acts may be provided. For example, act 30 is not performed, such as where the mini-emission imaging system 14 is already calibrated (i.e., the calibration does not need to occur for each patient and may be performed once or once per week, month, or year). As other examples, acts for placing the syringe 24 or vial in the cavity 26, removing the syringe 24 or vial, and/or injecting the patient are provided. In another example, acts for configuring for scanning the syringe 24 or vial, such as acts for selecting a PET or SPECT configuration, collimator, and/or scan process, are provided.

In act 30, the mini-nuclear or emission imaging system 14 is calibrated. A standardized, calibrated radiation source is placed in the cavity 26. The source has a known activity, dose, and/or isotope, such as a source from the National Institute of Standards and Technology (NIST). The emission imaging system detects emissions from the source. The detection may use a fixed geometry, such as the geometry to be used for measuring injected dose. Where there are multiple possible geometries, then multiple calibrations are determined by detecting emissions for each of the geometries.

The dose is determined using the measured activity over time by the detector 22. The measured dose is compared with the known dose of the source. The difference is used as a weight or a weight is looked up based on the difference so that the calculated dose from the detected emissions is correct (i.e., equal to the known dose of the source). For example, the amplitude and/or distribution represented in the dose model is adjusted. As another example, the calibration provides an adjustment or weighting for measured uptake. The measured uptake is adjusted to be more accurate based on the calibration. Different calibration may be provided for geometries and/or isotope.

Since a solid-state detector 22 is used in the mini-emission imaging system 14, the calibration may be performed periodically rather than for each patient. Any frequency of calibration may be used.

In act 32, the mini-emission imaging system 14 measures the activity of a radiopharmaceutical in a syringe 24 or vial. The syringe 24 or vial holding the radiopharmaceutical to be injected into the patient is placed in the cavity 26. The cavity 26 is sized to hold the syringe 24 or vial and may be small such that a patient cannot be placed in the cavity 26. This measurement is of the activity and/or dose for the isotope being used in the patient. After sealing the syringe 24 or vial in the cavity 26 (e.g., placing a lid over the cavity 26), the emissions are detected as the measure of activity.

To measure the activity, a PET or SPECT scan is performed. The mini-nuclear imaging system 14 scans for emissions from the radiopharmaceutical in the syringe 24 or vial. In one embodiment, the activity in the syringe 24 or vial is directly measured by the semiconductor detectors in a single measurement by combining direct photon measurements (e.g., spectrum and number of counts per energy bin) and extra modal information of the syringe or vial given another device, i.e., a camera, IR camera/sensor, etc.). A CT scan is not needed since there is a limited number of syringes or vials and an AI algorithm, for instance, can identify which syringe is being used and its position inside the chamber for precise activity calculation in the syringe pre- and post-injection for every patient. The measurement using the mini-nuclear imaging system 14 scans the radiotracer before and after injecting it in the patient, but after that, the PET/SPECT scanner 12 scans the patient. Multiple scans are performed over time for the patient. Using this approach, fewer scans and/or more accurate dose estimation will occur. Multiple sets of emissions from the patient are detected at multiple timepoints. Separate scans are used for each of the timepoints. Emissions are detected, such as with a complete SPECT or PET scan, for each of the timepoints. Where the same syringe 24 or vial is used multiple times (for the same patient or different patients), the later occurring uses already have activity measured, so the measurement to determine injected activity occurs after injection for the subsequent patient.

The emission imaging system 14 detects emissions from the radiopharmaceutical in the syringe 24 or vial with the detector 22 over time, such as over tens of seconds. A collimator in front of the detector 22 limits the direction of photons detected by the detector 22, so each detected emission is associated with an energy and line or cone of possible locations from which the emission occurred for SPECT scanning. The lateral position of the line or cone relative to the detector may likewise be determined. For PET scanning, coincidence processing may be used to detect a line of response for co-occurring emissions traveling in generally opposite directions. In alternative embodiments, the detection is performed without location determination (e.g., without a collimator). The counts are integrated into a global activity provided without spatial reconstruction (i.e., pseudo-imaging approach).

For the SPECT or PET scan, raw emission data is used for reconstruction. The reconstruction may use a system matrix or projection operators to describe the properties of the mini-emission imaging system to iteratively improve a data model of an image object representing the activity. The detected emissions are reconstructed to show spatial distribution of activity. Where the dose is reconstructed, activities over the different time points are used to reconstruction dose. The activities are reconstructed as part of reconstruction of the dose.

The image object, which is defined in an object or image space, is a reconstruction from the emission data measured in a data space. The object space is the space in which the result of the image reconstruction is defined and corresponds, for example, to the 3D volume or 2D area (i.e., field-of-view or "FOV") that is imaged. The detected emissions form projections, which may be tomographically computed to represent two- or three-dimensional distribution by reconstruction. The reconstruction uses emissions detected from different directions or camera locations in each set of emissions.

The tomographic reconstruction iteratively fits the detected emissions to a distribution of the radiopharmaceutical in object or image space. Iterative optimization is applied to find the distribution that best fits the measured emissions. Backward and forward projection from the detection space and the object space are used as well as any modeling, such as the system model for the emission tomography system (e.g., detector sensitivity) and/or a parametric dose model for kinetics of the radio tracer (e.g., diffusion in two directions (e.g., k1 and k2) with decay). In an iterative optimization, a model of the emission tomography system is used to forward project measurements to object space, and residuals are back projected for correcting a data model for the next iteration.

In act 34, the mini-nuclear imaging system 14 measures the activity in the syringe 24 or vial after injection. Act 32 is preformed prior to injection. The syringe 24 or vial is returned to the cavity 26 after injection of the radiopharmaceutical into the patient. The activity of any radiopharmaceutical remaining in the syringe 24 or vial after injection is measured. For dose determination, the activity is measured at different time points (i.e., multiple emission scans are performed over time). The activity of the remaining amounts of radiopharmaceutical is measured.

In act 36, the image processor determines the injected dose (activity). The injected dose is determined from the measured activity in the syringe 24 or vial before and after injection. The measured activities of acts 32 and 34 are used. The dose (activity) before injection is determined, and the dose (activity) after injection is determined. The difference in doses (activities) is the injected dose. The dose (activity) is determined without a dose calibrator. By using detected emissions from the solid-state detector 22, inaccuracies due to the non-linear response of a gas chamber may be avoided.

Where the measurements of activity in acts 32 and 34 are of the emissions, then reconstruction of the activity and/or dose is performed to determine the dose. The dose may be determined in one reconstruction from emissions from the multiple time points. The reconstruction is parametric, including a dose model fit as part of the reconstruction. Where activity is reconstructed in acts 32 and 34, then the dose is determined from the activity over time by fitting a dose model to the reconstructed activity over time.

To determine actual dose, a dose model is fit to the measured activity. This dose model is fit to reconstructed activity or fit in parametric reconstruction from the emissions. The dose model is fit to the activity measured prior to injection. The same or different dose model is fit to the activity measured after injection. The pre and post injection doses are derived from the fit dose models. The difference between the pre and post dose is the injected dose.

Any dose model may be used. The dose model may be a parametric model of pharmaceutical kinetics, such as diffusion, isotope half-life, biological half-life, and/or another characteristic of change over time in dosage being applied from the radiopharmaceutical. A physics model, such as using Monte Carlo, dose kernels as the model, or a transport model may be used to model emission probability and/or interaction for dose. Based on fitting, values of the model parameters of the dose model are solved, providing dose for any time and/or total dose for the locations of the distribution. As an example of a transport-based dose model, a 2-compartmental model is encapsulated in a set of linear differential equations, whereby the k12, . . . are kinetic parameters for moving from compartment 1 to compartment 2. Generally, the compartment can be a voxel or a volume of interest (VOI). By solving for the fit of the model of radiopharmaceutical kinetics, the dose may be determined. The dose or dose distribution is determined. The distribution is by voxel.

Figure 4:
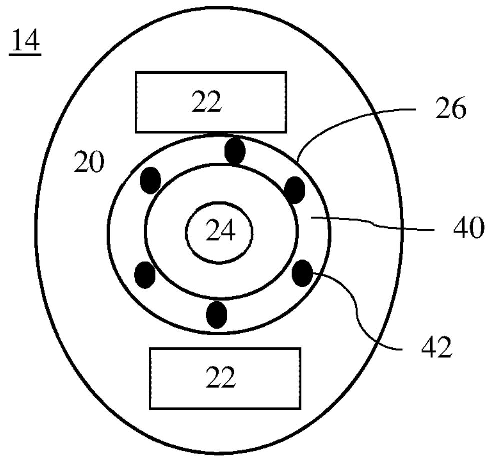
FIG. 4 is a cross-section top view of a miniaturized emission system with a tissue mimicking object having solid-state dosimeters for dose model calibration.

The mini-nuclear imaging system 14 may be used to calibrate the dose model used in reconstructing the injected and/or internal dose. FIG. 4 shows the mini-nuclear imaging system 14 with a tissue mimicking object 40 included in the cavity 26. The tissue mimicking object 40 mimics tissue of interest, such as blood, soft-tissue, or bone. For example, a water bath is used for blood. As another example, soft-tissue or bone mimicking plastic is used. Multiple objects 40 for multiple different tissues may be used. One object 40 may mimic different tissues. The object 40 has known attenuation and/or attenuations corresponding to the tissue being mimicked.

The tissue mimicking object 40 is positionable within the cavity 26. The object 40 has a known position and orientation. As shown in FIG. 4, the tissue mimicking object 40 has an outer surface sized and shaped to confirm with the surface of the cavity 26. In other embodiments, the tissue mimicking object 40 fits with less or no contact with the side walls, bottom, and/or top of the cavity 26, such as being held in the cavity 26 by one or more spacers or holders.

The tissue mimicking object 40 includes one or more solid-state dosimeters 42. For example, diamond detectors are used as the solid-state dosimeters 42. Other semiconductor detectors for directly measuring the dose may be used. Any number and any spacing of the dosimeters 42 may be provided.

The tissue mimicking object 40 includes an inner chamber into which the syringe 24 or vial is placed and held. The solid-state detectors 22 are used to measure activity, from which dose is determined. The dosimeters 42 measure the dose from the syringe 24 or vial at a same time or times as the detectors 22 detect emissions or over an equal but different period.

The image processor 16 calibrates the dose model using any difference in doses. The estimated dose from emissions is compared to the directly measured dose from the dosimeters 42 of the tissue mimicking object 40. The dose model is weighted or adjusted to result in the directly detected dose from the dosimeters 42 given the measured activity from the detectors 22. The dose mode is calibrated from the signals from the solid-state dosimeter 42.

FIG. 5 shows a flow chart diagram of a method for calibration of a dose model in nuclear imaging. The tissue mimicking object 40 and included dosimeter 42 are used to calibrate the transport, physics, or dose kernel-based dose model used for determining the internal dose of the patient. The mini-nuclear imaging system 14 allows for calibration of the dose model used for the patient.

The acts are performed in the order shown (numerical or top to bottom) or another order. For example, acts 50 and 54 are performed simultaneously or sequentially with act 50 first or with act 54 first. As another example, act 59 is performed after any of the acts and before act 58.

Additional, different, or fewer acts may be used. For example, act 58 and/or act 59 are not performed. As another example, acts for emission scanning a patient, such as with PET or SPECT imaging system 12 and/or acts for imaging anatomy by the anatomy imager 13 for multi-modal reconstruction and/or attenuation are performed. In yet another example, acts 50-56 are repeated for each of different types of tissue. Different tissue mimicking tissue mimicking objects 40 are used to calibrate the dose model by tissue type.

In act 50, the solid-state detectors 22 detect emissions from the radiopharmaceutical to be injected into a patient. The syringe 24 or vial is placed in the cavity 26 and in or beside the tissue mimicking object 40. The activity is measured by the detectors 22 while the tissue mimicking object 40 is in the mini-nuclear imaging system 14 with the syringe 24 or vial. Alternatively, the activity is measured without the tissue mimicking object 40 being in the cavity.

In act 52, the image processor determines the dose from a reconstruction of activity over time of the detected emissions. A representation of the object 40 is reconstructed from the detected emissions. The known attenuation and position of the object 40 may be used in the reconstruction. The activity distribution may be reconstructed for different times and the dose model fit to the reconstructed activity over time. Alternatively, parametric reconstruction is performed to fit the dose model to the activity from emissions over time. In yet other embodiments, activity from one time is used to fit the dose model.

The dose model of the time activity curve is fit to the emissions over time to compute the dose (e.g., energy/mass or J/kg (Gy)). For actual dose estimation, the dose function, D, is a function of time and is different from activity, A=Bq. For dose tomography (i.e., fitting the dose model as part of one reconstruction), the available data from the 1 . . . N timepoints are used to describe a dynamic process and specify what moment of the spatial distribution is desired. The 1 to N timepoints are used in one reconstruction to parametrize dose distribution. Instead of computing the quantitative activity at each time point, the tomographic data from multiple (e.g., all) available time points is used to directly reconstruct the dose. For example, a spatio-temporal inconsistent SPECT, where the tomographic dwell time the dwell T_D<<T_R (residence time of the radiopharmaceutical) and assuming that the activity is constant or only slowly changing over T_D as compared to T_R, measures at the different timepoints. The dose in the target volume is reconstructed directly in a parametric approach. In this parametric reconstruction approach, the error propagation is seamless, and the noisy voxels at the later times are naturally stabilized. This parametric approach provides a fit model of dose, that may extend to temporal consistent nuclear imaging systems and T_D<< or just < than T_R.

In an alternative embodiment, the spectrum information from the detected emissions is used to determine the isotope. The dose is estimated from the isotope and the emissions without reconstruction. Interpolation may be used to determine the dose from the spectrum.

In act 54, the solid-state dosimeters 42 of the tissue mimicking object 40 measure the dose of the syringe 24 or vial. The tissue mimicking object 40 is in the cavity 26 with the syringe 24 or vial to measure the dose. The image processor 16 uses the signals from the solid-state dosimeters 42 to determine the dose for a same length of time as the dose determined in act 52.

In act 56, the image processor 16 calibrates the dose model with the measured dose from the solid-state dosimeter 42 and the estimated dose derived from the emissions detected by the solid-state detectors 22. The dose model is a physics, dose kernel, or transport (transfer) model. One or more values or weights of the dose model are set based on a difference between the estimated dose and the measured dose. An optimization may be performed to set multiple variables based on the difference in dose. The optimization minimizes the difference between the doses.

In other embodiments, the measured dose and the isotope from the spectrum of the emissions is used to calibrate the dose model. A library of dose models is provided for different isotopes and measured dose. By selecting or interpolating, a dose model calibrated for the isotope and tissue being mimicked is selected.

The calibrated dose model more likely provides accurate dose estimation from measured emissions for a given radiopharmaceutical and corresponding isotope. Rather than using an uncalibrated or general dose mode, the calibration provides for more accurate dose estimation with the calibrated dose model.

In act 58, the image processor or another processor calculates an internal dose for a patient with the injected dose. After injecting the patient with the injected dose, the patient is scanned. Emissions are detected, such as with PET or SPECT. The resulting emissions are used to determine the dose over a given time or treatment. The dose by voxel and/or organ (i.e., tissue type) may be determined.

This internal dose is calculated using the dose model as calibrated. The dose model may be incorporated into reconstruction to reconstruct the dose. Alternatively, the dose model is fit to activity or uptake reconstructed at different times. The fit dose model is used to calculate the dose. The dose model and/or reconstruction may use the injected dose as a variable. Based on the injected dose and the calibrated dose model, the internal dose for the patient is determined.

The scan by the mini-nuclear imaging system 14 may be used to simplify scanning the patient and/or to confirm accurate entry of information. In act 59, the image processor determines the isotope used in the radiopharmaceutical. The isotope information is typically entered manually. Since the detectors 22 are solid-state, a spectrographic measurement is performed. This spectrum information may be used to determine the isotope. The spectrum is used to look-up the isotope. A fitting approach may be used where the spectrum is fit to spectra of possible isotopes or mixes of isotopes. The image processor confirms the isotope entry or directly enters the isotope without user input.

Similarly, the scan may indicate the form factor for the syringe 24 or vial. In act 59, the image processor determines the form factor. Different form factors may be used, which provides for different volumes. The distribution of activity from the detected emissions is used to determine the form factor, such as with a classifier (e.g., artificial intelligence-based classifier). This form factor information may be directly entered without user input or the user input form factor may be confirmed.

In alternative embodiments, RFID, bar codes, or a detector (e.g., artificial-intelligence-based detector) uses camera images or other scans to identify the isotope, form factor, and/or patient. The isotope, patient, dose, application of the nuclear imaging, and/or other information are automatically detected, such as from a label on the syringe 24, and integrated for determining internal dose and/or linked to the patient or nuclear imaging system. This information may not need to be manually input, reducing the burden on the operator.

In one embodiment, using the mini-nuclear imaging system, quantitative tomography is used tom compute the activity in volume of the syringe or vial (e.g., mCl or MBq as decay/second) to be delivered to the patient. Since the mini-nuclear imaging system is used, the spectroscopic performance may identify the isotope or mix of isotopes to apply the calibrations and then prepare for the link between activity of isotope and dose measured at certain physical locations in the patient. In a workflow, the activity in the syringe-is measured tomographically. The spectrum information may account for details of the container (form factor) and any materials surrounding the radiopharmaceutical when performing dosimetry measurements. The dose (activity in volume) is measured and the dosimetry calculation is used to calibrate what was measured. A self-consistent and/or calibratable set of information (e.g., activity of isotope in syringe and isotope being used) is provided using the imaging scan and such information may be used for dosimetry (energy deposition in the patient). Because the specific properties are provided by the spectroscopic resolution and spatial resolution, the identification of the isotope is automatically determined for dose estimation.

The image processor generates an image of the dose of the syringe 24 or vial, activity distribution of the syringe 24 or vial, dose of the patient, and/or activity distribution of the patient. Any now known or later developed imaging for quantitative nuclear imaging may be used. After reconstruction, the output image object of dose distribution at a particular time, for a cycle, up to the current time, up to a last scan, and/or predicted for the not-yet occurring end of cycle is generated.

The image object is rendered or otherwise used to generate an image. For example, a multi-planar reconstruction or single slice image of a plane is generated. The intersection of one or more planes with the image object is visualized. As another example, a surface or projection rendering is performed for three-dimensional imaging. Other imaging may be used.

One image is generated. Alternatively, a sequence of images is generated. For example, image objects of dose at different time periods are used to generate a sequence of images representing the dosing in the patient over time.

The dose image of the functional information from the reconstruction is displayed alone. Alternatively, an anatomical image is displayed with the functional image. For example, the functional image is overlaid on a CT image. The overlay may be dose colored for display on a gray scale CT image. Other combinations may be used, such as accumulated dose, uptake at a timepoint, and a CT image. An image of dose distribution and quantitative uptake may be generated and displayed.

For quantitative SPECT or PET, the image may be an alphanumeric text of a dose value for a location or a global dose. A graph, chart, or other representation of dose at multiple locations and/or times may be output. The spatial image representing distribution of dose may use color or brightness modulation to represent a level of dose by location. In one embodiment, the image is generated to show the average quantitative uptake by type of tissue.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for determining injected dose, the method comprising:

measuring first activity of a radiopharmaceutical in a syringe or vial by (a) performing a first tomographic scan of the radiopharmaceutical in the syringe or vial by a nuclear imaging system having a solid-state detector and sized to scan the syringe or vial without fitting a patient and (b) reconstructing the first activity from first emissions detected in the first tomographic scan;

measuring second activity of remaining amounts of the radiopharmaceutical in the syringe or vial after injection into the patient by (a) performing a second tomographic scan of the remaining amount of the radiopharmaceutical in the syringe or vial by the nuclear imaging system and (b) reconstructing the second activity from second emissions detected in the second tomographic scan; and determining an injected activity from the first activity and the second activity.

2. The method of claim 1 wherein measuring the first and second activities comprises measuring with the solid-state detector comprising semiconductor material.

3. The method of claim 1 wherein measuring the first and second activities comprises measuring by the nuclear imaging system being sized to fit the syringe or vial in a hole less than 3 inches by 3 inches.

4. The method of claim 1 wherein measuring the first and second activities comprises measuring by the nuclear imaging system having at least one handle and being sized to be carriable by a person using the handle.

5. The method of claim 1 wherein determining the injected activity comprises determining without a dose calibrator.

6. The method of claim 1 wherein measuring the first and second activities comprises measuring the first activity over time and measuring the second activity over time, and wherein determining the injected activity comprises fitting a first model to the first activity over time, fitting a second model to the second activity over time, deriving a first dose from the first model as fit and a second dose from the second model as fit, and determining the injected activity from a difference between the first and second doses.

7. The method of claim 1 further comprising calibrating the nuclear imaging system from emission detection from a standardized source in the nuclear imaging system.

8. The method of claim 1 wherein measuring the first activity comprises measuring the first activity where a tissue mimicking object including a solid-state dosimeter is in the nuclear imaging system with the syringe or vial, and further comprising measuring a first dose with the solid-state dosimeter.

9. The method of claim 8 further comprising calibrating a dose model for the radiopharmaceutical with the first dose.

10. The method of claim 9 wherein the dose model is one of a physics model, dose kernel model, or transfer model.

11. The method of claim 1 further comprising calculating an internal dose for a patient with the injected dose.

12. The method of claim 1 wherein measuring the first activity comprises performing an emission scan by the nuclear imaging system of the radiopharmaceutical and the syringe or vial, and further comprising determining an isotope and form factor for the syringe or vial from the emission scan.

13. A dosimeter for medical nuclear imaging, the dosimeter comprising:

a cavity configured to hold a syringe or vial;

a semiconductor detector adjacent the cavity and configured to detect emissions from within the syringe or vial within the cavity; and an image processor configured to determine a dose for the syringe or vial from a reconstruction of activity in the syringe or vial, the reconstruction being from the emissions detected by the semiconductor detector.

14. The dosimeter of claim 13 wherein the cavity has an opening of 3 inches by 3 inches or less through which the syringe or vial is placeable into the cavity.

15. The dosimeter of claim 13 wherein the semiconductor detector comprises a pair of solid-state detectors on opposite sides of the cavity.

16. The dosimeter of claim 13 further comprising a tissue mimicking object with a solid-state dosimeter, the tissue mimicking object positionable within the cavity, and wherein the image processor is configured to calibrate a dose model from signals from the solid-state dosimeter.

17. A method for calibration of a dose model in nuclear imaging, the method comprising:

detecting emissions from a radiopharmaceutical to be injected into a patient with a solid-state detector, the radiopharmaceutical being within a cavity adjacent to the solid-state detector during the detecting;

measuring a first dose with a solid-state dosimeter in a tissue mimicking object, the tissue mimicking object in the cavity during the detecting and measuring; and calibrating the dose model with the first dose from the solid-state dosimeter and a second dose derived from the emissions.

18. The method of claim 17 further comprising determining the second dose from a reconstruction of activity over time of the detected emissions, and calculating an internal dose for a patient after injection of the radiopharmaceutical, the internal dose calculated with the dose model as calibrated.

19. A method for determining injected dose, the method comprising:

imaging a radiopharmaceutical in a syringe or vial with a nuclear imaging system having a solid-state detector;

computing activity of the radiopharmaceutical in the syringe or vial from the imaging;

determining an isotope of the radiopharmaceutical in the syringe or vial from the imaging of the radiopharmaceutical in the syringe or vial; and estimating dose in a patient based on the activity and the isotope.

* * * * *